United States Patent [19]

Kroll

[11] Patent Number: 5,522,853

[45] Date of Patent: *Jun. 4, 1996

[54] METHOD AND APPARATUS FOR PROGRESSIVE RECRUITMENT OF CARDIAC FIBRILLATION

[75] Inventor: Mark W. Kroll, Minnetonka, Minn.

[73] Assignee: Angeion Corporation, Plymouth, Minn.

[*] Notice: The term of this patent shall not extend beyond the expiration date of Pat. No. 5,366,485

[21] Appl. No.: 344,281

[22] Filed: Nov. 21, 1994

Related U.S. Application Data

[63] Continuation-in-part of Ser. No. 967,215, Oct. 27, 1992, Pat. No. 5,366,485, Ser. No. 993,292, Dec. 18, 1992, Pat. No. 5,383,907, Ser. No. 96,170, Jul. 22, 1993, Pat. No. 5,441,518, and Ser. No. 132,634, Oct. 6, 1993.

[51] Int. Cl.⁶ .................................................. A61N 1/39
[52] U.S. Cl. ............................................................ 607/5
[58] Field of Search ...................................... 607/5, 6, 7, 8

[56] References Cited

U.S. PATENT DOCUMENTS

| | | |
|---|---|---|
| 3,211,154 | 10/1965 | Becker et al. |
| 3,241,555 | 3/1966 | Caywood et al. |
| 4,025,860 | 5/1977 | Shibata et al. |
| 4,530,550 | 7/1985 | Kondo |
| 4,637,397 | 1/1987 | Jones et al. |
| 4,638,397 | 1/1987 | Jones et al. |
| 4,708,145 | 11/1987 | Tacker et al. |
| 4,727,877 | 3/1988 | Kallok |
| 4,800,883 | 1/1989 | Winstrom |
| 4,821,723 | 4/1989 | Baker, Jr. et al. |
| 4,850,337 | 7/1989 | Bach, Jr. |
| 4,931,947 | 6/1990 | Werth et al. |
| 4,969,463 | 11/1990 | Dahl et al. |
| 4,996,984 | 3/1991 | Sweeney |
| 4,998,531 | 3/1991 | Bocchi et al. |
| 5,052,407 | 10/1991 | Hauser et al. |
| 5,107,834 | 4/1992 | Idecker et al. |
| 5,163,427 | 11/1992 | Keimel ........................................ 607/4 |
| 5,199,429 | 4/1993 | Kroll et al. |
| 5,209,229 | 5/1993 | Gilli |
| 5,306,291 | 4/1994 | Kroll et al. |

FOREIGN PATENT DOCUMENTS 0280526  8/1988  European Pat. Off. .................. 607/5

OTHER PUBLICATIONS

Schuder, J. C. et al. Transthoracic Ventricular Defibrillation with Square–Wave Stimuli: One–Half Cycle, One Cycle andMultiCycle Waveforms, Circulation Research, 1964; 15: 258–264.

Kavanagh, K. M. et al., Comparison of the Internal Defibrillation Thresholds for Monophasic and Double and Single Capacitor Biphasic Waveforms, J. American College of Cardiology, 1989; 14:1343–1349.

Ser. No. 07/856982 to Adams et al.

Kroll M. W. et al., Decline in Defibrillation Thresholds, PACE 1993; 16#1:213–217.

(List continued on next page.)

*Primary Examiner*—William E. Kamm
*Assistant Examiner*—Scott M. Getzow
*Attorney, Agent, or Firm*—Patterson & Keough

[57] ABSTRACT

A method and apparatus for progressive recruitment of cardiac fibrillation uses an implantable defibrillator to deliver a multiple, discontinuous pulse waveform that is comprised of a series of smaller recruitment pulses delivered prior to delivery of a larger defibrillating pulse. Instead of using multiple identical pulses to accomplish defibrillation, the present invention decreases the overall energy required for effective defibrillation with a single, larger defibrillation pulse by using multiple, smaller recruitment pulses to recruit or capture as many heart cells as possible into a primary one of the many activation wavefronts in a fibrillating heart. By synchronizing the heart cells recruited in this manner, the effectiveness of the single, larger defibrillation pulse is increased, thereby decreasing the maximum stored energy required for defibrillation.

33 Claims, 7 Drawing Sheets

OTHER PUBLICATIONS

Bardy, G. H. et al. A Prospective Fandomized Evaluation of Biphasic vs. Monophasic Waveform Pulses on Defibrillation Efficiency in Humans, J. American College of Cardiology, 1989 14:728–733.

Wyse, D. G. et al., Comparison of Biphasic and Monophasic Shocks for Defibrillation using a Non–Thoracotomy System, American J. Cardiology 1993; 71: 197–202.

Freeser, S. A. et al., Strength–Duration and Probability of Success Curves for Defibrillation with Biphasic Waveforms, Circulation, 1990; 82:2128–2141.

Walker R. G., Walcott G. P., Swanson D. K. et al., Relationship of Charge Distribution between Phases in Biphasic Waveforms, Circulation 1992; 86 No. 4:I–792 (Abstract).

Gurvish H. L., Markarychev, V. A.: Defibrillation of the Heart with Biphasic Electrical Impulses, Kardiologilia 1967;7:109–112.

Tchou P., Krum D., Aktar M. Avitall B., Reduction of Defibrillation Energy Requirements with new Biphasic Waveforms, PACE 1990; 13:507 (Abstract).

Jones J. L., Jones R. E., Balasky G., Improved Cardiac Cell Excitation with Symmetrical Biphasic Defibrillator Waveforms, American J. Physiology 1987; 253:H1418–H1424.

Kavanagh K. M., Duff H. J., Clark R., et al., Monophasic vs. Biphasic Cardiac Stimulation: Mechanism of Decreased Energy Requirements, PACE 1990:13; 1268–1276.

Swartz J. F., Jones J. L., Jones R. E., Fletcher R. D., Conditioning Prepulse of Biphasic Defibrillator Waveforms Enhances Refractoriness to Fibrillation Wavefronts, Circulation Research 1991;68:438–449.

Karasik P., Jones R., Jones J., Effect of Waveform Duration on Refractory Period Extension Produced by Monophasic and Biphasic Defibrillator Waveforms, PACE 1991; 14:715 (abstract).

Tang ASL, Yabe S., Wharton J. M. et al., Ventricular Defibrillation Using Biphasic Waveforms: The Importance of Phasic Defibrillation, J. American College of Cardiology 1989; 13:207–14.

Bourland J. D., Tacker W. A., Geddes L. A. et al., "Comparative Efficacy of Damped Sign Wave and Square Wave current for Transchest Ventricular Defibrillation in Animals", Medical Instrumentation 1978;12#1:38–41.

Irnich W., "The Chronaxie Time and its Practical Importance", PACE 1980; 8:870–888.

Kroll M. W., Adams T. P., "The Optimum Pulse Width for the Implantable Defibrillator", 7th Purdue Conference on Defibrillation, American Heart Journal 1992; 124#3,835.

Schwartz J. F., Karasik P. E, Donofrio J. et al., "Effect of Biphasic Waveform Tilt on Human Non–Thoracotomy Defibrillation Threshold", PACE 1993;16#4II:888.

Ideker R. E., Tang A. S. L., Frazier D. W. et al., "Ventricular Defibrillation: Basic Concepts":, Cardiac Pacing and Electrophysiology 3rd Ed., edited by El–Sherif N. & Samatt, W. B. Saunders Co. Philadelphia 1991;42:713–726.

Frazier D. W., Wolf P. D., Wharton J. M., et al., "A Stimulas Induced Critical Point: A Mechanism for Electrical Initiation of Re–Entry in Normal Canine Myocardium", J. of Clinical Investigation 1989;83:1039.

Shibata N., Chen P. S., DIxon E. G., et al., "Epicardial Activation Atter Unsuccessful Defibriallation Shocks in Dogs", American J. Physiology 1988;255:H902–H909.

Zhou X. Daubert J. P., Wolf P. D., et al., "Epicardial Mapping of Ventricular Defibrillation with Monophasic and Biphasic Shocks in Dogs":, Circulation Research 1993;72:145–160.

Jones J. L., Jones R. E., "Decreased Defibrillator–Induced Dysfunction with Biphasic Rectangular Waveforms", American J. Physiology 1984:247:H792–796.

Niebauer M. J., Babbbs C. F., Geddes L. A., et al., "Efficacy and Safety of the Reciprocal Pulse Defibrillator Current Waveform", Medical and Biological Engineering and Computing 1984;22:28–31.

Kavanagh, K. M. et al., Comparison of the Internal Defibrillation Thresholds for Monophasic and Double and Single Capacitor Biphasic Waveforms, J. American College of Cardiology, 1989; 14:1343–1349.

Feeser S. A., Tang A. S. L., Kavanagh K. M., et al., "Strength—Duration and Probability of Success Curves for Defibrillaion with Biphasic Waveforms". Circulation 1990;82:2128–2141.

Dixon E. F., et al., "Improved Defibrillaion Thresholds with Large Contoured Epicardial Electrodes and Biphasic Waveforms", Circulation, 1987;76:1176–1184.

Chapman, et al., "Efficacy of Monophasic and Biphasic Truncated Exponential Shocks for Nonthoracotomy Internal Defibrillation in Dogs", J. American College of Cardiology, 1988;12:739–745.

Dillon S. M., "Synchronized Depolarized after Defibrillation Shocks: A Possible Component of the Defibrillation Process Demonstrated by Optical Recordings in Rabbit Heart", Circulation 1992;85:1865–1878.

Sweeney R. J., et al., "Ventricular Refractory Period Extension Caused by Defibrillation Shocks", Circulation 1990;82:965–972.

Belz M. K. et al., "Successful Defibrillation Prolongs Action Potential Durations in Humans", PACE 993;16:932.

Frasier D. W. et al., "Extracellular Field Required for Excitation in Three–Dimensional Anisotropic Canine Myocardium":, Circulation Reserach 1988;63:147–164.

Wessale J. L. et al., "Bipolar Catheter Defibrillation in Dogs using trapezoidal Waveforms of Various Tilts", J. Electrocardiology 1980;13(4):359–366.

Wharton J. M. et al., "Electrophysiological Effects in Vivo of Monophasic and Biphasic Stimuli in Normal and Infarcted Dogs", PACE 1990;13:1158–1172.

Niebauer M. J., Babbbs C. F., Geddes L. A., et al., "Efficacy and Safety of Defibrillation with Rectangular Waves of 2 to 20–milliseconds Duration", Crit. Care Medicine 1983; 11#2:95–98.

Daubert J. P. et al., "Response of Relatively Refractory Canine Myocardium to Monophasic and Biphasic Shocks", Circulation 1991;84:2522–2538.

Zhou X. Daubert J. P., Wolf P. D., et al., "Prolongation of Repolorization Time by Electric Field Stimulation with Monophasic and Biphasic Shocks in Open Chest Dogs", Circulation Research 1991;68:1761–1767.

Yabe S., et al., "Conduction Disturbances Caused by High Current Density Electric Fields", Circulation Reserach 1990;66:1190–1203.

Fozzard H. A., "Membrane Capacity of the Cardiac Purkinje Fiber", J. physiol (Great Britian) 1966; 182:255–267.

Weidmann S., "Electrical Constants of Trabecular Muscle from Mammalian Heart", J. Physiol (Great Britian) 1970;210:1041–1054.

Knisley S. B. et al., "Optical Measurement of Transmembrance Potential Changes During Electric Field Stimulation of Ventricular Cells", Circulation Research 1993;72:255–270.

January C. T. et al., "Early After Depolarization Newer Insights into Cellular Mechanisms"; J. Cardiovascular Electrophysiology 1990;1:161–169.

Shibata N. et al., "Epicardial Activation After Unsuccessful Defibrillation Shocks in Dogs", American J. Physiology 1988;255:H902–909.

Chen P. S. et al., "Epicardial Activation During Ventricular Defibrillation in Open–Chest Dogs", J. Clinical Investigation 1986;77:810–823.

Cooley J. W., Dodge F. A., "Digital Computer Solutions for Excitation and Propagation of the Nerve Impulse", Biophysical Journal 1966;6:583–599.

Krassowska W., et al., "Propagation vs. Delayed Activation During Field Stimulation of Cardiac Muscle", PACE 1992;15:197–210.

Schwartzman D. et al., "Serial Patch—Patch Impedence Values in an Epicardial Defibrillation System", PACE 1993;16:916.

Cooper R. et al., "The Effect of Phase Separation on Biphasic Waveform Defibrillation", PACE, vol. 6, Mar., Part I, 1993.

Kao C. Y., Hoffman B. F., "Graded and Decremental Response in Heart Muscle Fiber", American J. Physiology 1958;194(1):187–196.

Kugelberg, J., "Ventricular Defibrillation with square-–waves," Scandinavian Society of Thoraci Surgery, Oct. 1965, pp. 123–128.

Sweeney et al, "Use of Fibrillation Cycle length to Effectively Combine Multiple Defibrillation Shocks", *Supp. II Cir.*, vol. 84, No. 4, Oct. 1991, Abst 2425.

Sweeney et al, "Defibrillation using a series of shocks timed to the fibrillation cycle length", *Am. Heart J*, vol. 128, No. 3, Sep. 1994, p. 638.

Johnson et al., "Defib. Efficacy for various delays between two successive biphasic shocks", *NASPE Abstracts: PACE*, Part II, vol. 14, No. 391, Apr. 1991, p. 715.

Manz. M. et al., "Can Triphasic Shock Waveforms Improve ICD Therapy in Man?", *Supplement to Cir.*, vol. 88, No. 4, Part 2, Oct. 1993 Abst 3192.

METHOD AND APPARATUS FOR PROGRESSIVE RECRUITMENT OF CARDIAC FIBRILLATION

RELATED APPLICATIONS

This application is a continuation-in-part application of four copending applications previously filed in the United States Patent and Trademark Office, the first of which was filed on Oct. 27, 1992 and entitled PROCESS FOR DEFIBRILLATION PRETREATMENT OF A HEART, Ser. No. 07/967,215, to be issued as U.S. Pat. No. 5,366,4875, the second of which was filed on Dec. 18, 1992 and entitled "SYSTEM AND METHOD FOR DELIVERING MULTIPLE CLOSELY SPACED DEFIBRILLATION PULSES", Ser. No. 07/993,292, now U.S. Pat. No. 5,383,907, the third of which was filed on Jul. 22, 1993 and entitled "IMPLANTABLE CARDIOVERTER DEFIBRILLATOR SYSTEM HAVING INDEPENDENTLY CONTROLLABLE ELECTRODE DISCHARGE PATHWAYS", Ser. No. 08/096,170, now U.S. Pat. No. 5,446,518 and the fourth of which was filed on Oct. 6, 1993 and entitled METHOD AND APPARATUS FOR GENERATING BIPHASIC WAVEFORMS IN AN IMPLANTABLE DEFIBRILLATOR, Ser. No. 08/132,634 pending, all of which are assigned to the assignee of the present invention and the disclosure of each of which is hereby incorporated in the present application.

BACKGROUND OF THE INVENTION

1. Field of the Invention

The present invention relates generally to implantable defibrillator systems, and more particularly, to a method and apparatus for progressive recruitment of cardiac fibrillation using an implantable defibrillator system.

2. Background of the Invention

Implantable defibrillator systems deliver a high voltage electrical countershock to the heart in an attempt to correct or convert a detected cardiac arrhythmia or fibrillation. Due to the limitations on size and power imposed by the fact that these systems must be self-contained implantable devices, all existing implantable defibrillator systems generate an electrical countershock by charging a capacitor system to a high voltage. The electrical charge stored in the capacitor system is then delivered as a truncated capacitive discharge through two or more implanted electrodes.

To date, there have been two basic kinds of truncated capacitive discharge waveforms implemented by commercially approved implantable defibrillator systems: monophasic waveforms and biphasic waveforms. Monophasic waveforms are comprised of a single monotonically decaying electrical pulse that is typically truncated before the capacitor system is completely discharged. Biphasic waveforms, on the other hand, are comprised of a pair of decaying electrical pulses or phases that are of opposite polarity. To generate a biphasic pulse, a first pulse or phase is discharged from the capacitor system in the same manner as a monophasic waveform and then, at the point the first pulse is truncated, an H-bridge switch circuit connected to the electrodes is used to immediately reverse the discharge polarity of the capacitor system as seen by the electrodes in order to produce the second pulse or phase of the biphasic waveform that is of the opposite polarity. A typical example of the use of an H-bridge circuit to generate a biphasic waveform in an implantable defibrillator system is shown in U.S. Pat. No. 4,998,531.

In addition to monophasic and biphasic defibrillation waveforms, there have been several forms of multiple pulse defibrillation waveforms which have been proposed. The idea of using multiple pulses for defibrillation has been experimented with since as early as 1965. An external defibrillator capable of delivering multiple pulses is shown in U.S. Pat. No. 3,211,154, issued to Becker et al. Ventricular defibrillation of dogs with a multiple pulse waveform was also disclosed in 1965 by Kugelberg. Kugelberg, J., "Ventricular Defibrillation with Square-Waves", *Scandinavian Society of Thoracic Surgery*, Oct. 1965, pgs. 123–28. In Kugelberg's experiment, two identical spaced-apart pulses were delivered as a defibrillation waveform having a pulse length and pulse interval adjusted so that those heart cells excitable at any given moment would be defibrillated by the first pulse and refractory to the second pulse.

Since the introduction of the concept of multiple pulse defibrillation waveforms, researchers have investigated the impact of various timing relationships and discharge pathways on defibrillation effectiveness when delivering a sequence of identical pulses. Sweeney and Reid disclose that the interaction between multiple identical pulses is non-linearly related to the fibrillation cycle length, and that the spacing between multiple pulses may be a fixed percentage of the spacing between fibrillation zero crossing in the heart. Sweeney et al., "Use of Fibrillation Cycle Length to Effectively Combine Multiple Defibrillation Shocks", *Supplement to Circulation*, Vol. 84, No. 4, Oct. 1991, Abst. 2425; and Sweeney, et al., "Defibrillation Using a Series of Shocks Timed to the Fibrillation Cycle Length", *American Heart Journal*, Vol. 128, No. 3, Sept. 1994, pg. 638. Johnson et al. disclose that successive biphasic pulses delivered through two different electrodes may be either beneficial or detrimental, depending upon the delay between the two pulses. Johnson et al., "Defibrillation Efficacy for Various Delays Between Two Successive Biphasic Shocks", *NASPE Abstracts: PACE*, Part II, Vol. 14, No. 391, Apr. 1991, p. 715.

Different techniques for the delivery of multiple identical pulse defibrillation waveforms have been proposed and include: a sequential pulse, multiple pathway waveform as shown in U.S. Pat. No. 4,708,145 issued to Tacker, Jr. et al. and U.S. Pat. No. 5,163,427 issued to Kiemel; multiple pulses with timing based on the fibrillation cycle length as shown in U.S. Pat. No. 4,995,986 issued to Sweeney; and a low energy multiple shock waveform as shown in U.S. Pat. No. 5,107,834 issued to Ideker et al. in which two waveforms of successively lover energy are used to defibrillate.

U.S. Pat. No. 4,637,397 issued to Jones et al. shows a triphasic defibrillation system in which two of the three multiple, adjacent phases of the waveform are generated so as to be a predetermined percentage of the discharge voltage of the primary defibrillation phase. The Jones reference, however, is more accurately characterized as a single pulse defibrillation waveform in the same way that a biphasic waveform is considered a single pulse due to the fact that successive phases of the waveform are delivered sequentially with essentially no delay between phases other than any delays inherent in the switching circuitry used to alternate the polarity of each phase of the waveform. In addition, the triphasic waveform suggested by Jones et al. has been shown to be no more effective than a traditional biphasic waveform. Manz, M. et al., "Can Triphasic Shock Waveforms Improve ICD Therapy in Man?", *Supplement to Circulation*, Vol. 88, No. 4, Part 2, Oct. 1993, Abst. 3193.

Although several different approaches have been proposed for multiple pulse defibrillation waveforms, to date, none of these approaches has resulted in a practical defibrillation waveform which has been shown to consistently reduce defibrillation thresholds and which could be successfully implemented in an implantable defibrillator system. It is believed that the lack of an accepted theory for exactly how multiple pulse defibrillation waveforms operate to correct a fibrillating heart has impeded further development and enhancement of the multiple pulse defibrillation waveform. Accordingly, it would be desirable to provide a method and apparatus for progressive recruitment of cardiac fibrillation using an implantable defibrillator system that arises out of an improved understanding of the nature and effect of a multiple pulse defibrillation waveform on the fibrillating heart.

SUMMARY OF THE INVENTION

The present invention is a method and apparatus for progressive recruitment of cardiac fibrillation by using an implantable defibrillator to deliver a multiple, discontinuous pulse waveform that is comprised of a series of smaller recruitment pulses delivered prior to delivery of a larger defibrillating pulse. Instead of using multiple identical pulses to accomplish defibrillation, the present invention decreases the overall energy required for effective defibrillation with a single, larger defibrillation pulse by using multiple, smaller recruitment pulses to recruit or capture as many heart cells as possible into a primary one of the many activation wavefronts in a fibrillating heart. By synchronizing the heart cells recruited in this manner, the effectiveness of the single, larger defibrillation pulse is increased, thereby decreasing the maximum stored energy required for defibrillation.

In accordance with a first embodiment of the present invention, an improved implantable defibrillator system produces a multiple pulse capacitive-discharge countershock to be delivered through at least two electrodes adapted for implantation in a human patient. The implantable defibrillator system is a self-contained human implantable housing containing a waveform-generating capacitor system for storing an electrical charge, a battery and transformer system for charging the waveform-generating capacitor system, a sensor arrangement for sensing a cardiac dysrhythmia in the human patient, and a controller for selectively discharging the electrical charge in the waveform-generating capacitor system as a countershock to be delivered through the at least two electrodes in response to the means for sensing the cardiac dysrhythmia. The improvement of the present invention include a controller for selectively discharging that includes a system for selectively discharging a plurality of recruitment pulses. Each recruitment pulse is spaced apart by a first time interval and delivers an electrical charge from the waveform-generating capacitor means that is less than a maximum recruitment charge. The controller also includes a system for selectively discharging a defibrillation pulse spaced apart by a second time interval from the plurality of recruitment pulses. The defibrillation pulse delivers an electrical charge that is greater than the maximum recruitment charge. The maximum recruitment charge is determined by an amount of electrical charge which the charging means can recharge the waveform-generating capacitor means during the second time interval.

In accordance with a second embodiment, a method for operating an implantable defibrillator device electrically connected to at least two electrodes adapted for implantation in a human patient treats cardiac dysrhythmia by delivering a multiple pulse capacitive-discharge countershock. The method comprises the device-implemented steps of first sensing for a cardiac dysrhythmia in a human patient. In response to sensing the cardiac dysrhythmia, a capacitive charge storage system within the implantable defibrillator device is charged to a charge value. Less than a first portion of the charge value stored in the capacitive charge storage system is selectively discharged through the at least two electrodes to produce a plurality of recruitment pulses, each recruitment pulse spaced apart by a first time interval. The capacitive charge storage system is recharged to the charge value after each recruitment pulse. After delivery of the recruitment pulses, more than the first portion of the charge value stored in the capacitive charge storage system is discharged through the at least two electrodes to produce a defibrillation pulse that is spaced apart by a second time interval from the plurality of recruitment pulses.

In accordance with a third embodiment, an implantable defibrillator apparatus electrically connected to at least two electrodes adapted for implantation in a human patient treats cardiac dysrhythmia by delivering a multiple pulse capacitive-discharge countershock. The implantable defibrillator apparatus comprises an implantable housing which contains a sensing system for sensing a cardiac dysrhythmia in the human patient, a capacitor system for storing an electrical charge, a power source system for charging the capacitor system to a charging voltage, and a control system for selectively controlling the power source system and the capacitor system in response to the sensing of the cardiac dysrhythmia to deliver a multiple pulse capacitive-discharge countershock to the at least two electrodes. The control system includes a system for selectively discharging a plurality of recruitment pulses, each recruitment pulse spaced apart by a first time interval and delivering an electrical charge that is less than a maximum recruitment charge. The control system also includes a system for selectively discharging a defibrillation pulse spaced apart by a second time interval from the plurality of recruitment pulses and delivering an electrical charge that is greater than the maximum recruitment charge.

DESCRIPTION OF THE PREFERRED EMBODIMENTS

In describing the preferred embodiments of the present invention, a description of the current models of understanding both fibrillation and defibrillation are presented. With these models in mind, a description of the theory behind the present invention is presented. Finally, specific implementations of the present invention are described.

Figure 1:
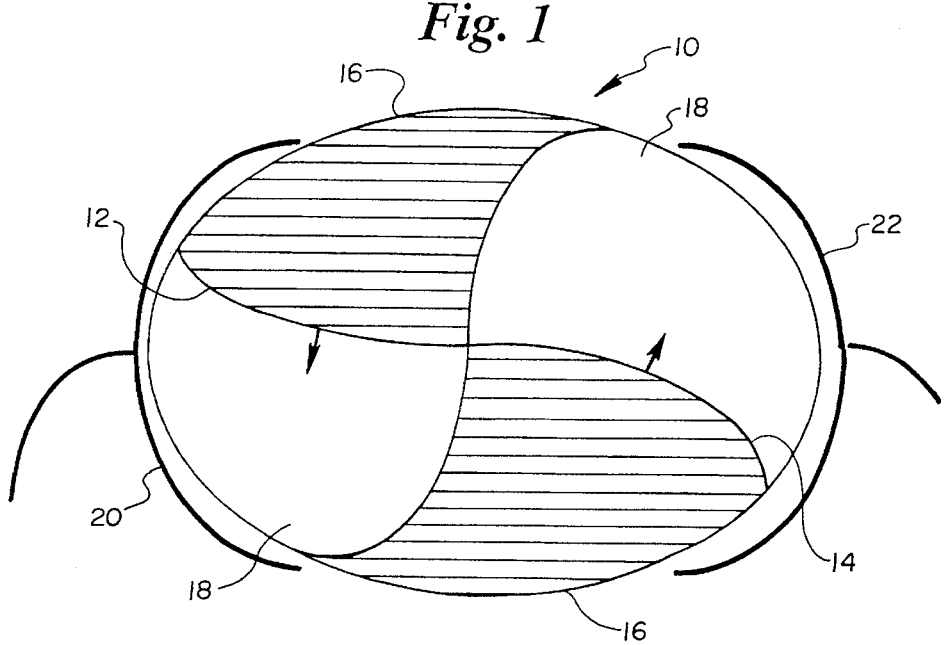
FIG. 1 is a stylized diagram of a fibrillating heart.

FIG. 1 shows a stylized diagram of a heart 10 which has a "dual wavefront" fibrillation pattern represented by multiple wavefronts 12, 14 of fibrillation activations. Unlike a normal sinus rhythm in which a single, organized activation wavefront cycles through heart 10 to properly stimulate the mechanical pumping action of the myocardium, in a fibrillation condition multiple, chaotic activation wavefronts course through heart 10 creating an uncoordinated response of the myocardium that is not capable of generating a perfusing pulse. In each wavefront 12, 14, a shaded region 16 represents heart cells that are activated while an unshaded region 18 represents heart cells that are resting and recovered or "repolarized". The arrows show the direction of rotation of each wavefront 12, 14 in the fibrillation pattern. While only a pair of wavefronts 12, 14 are shown in this stylized representation of a fibrillation pattern, it should be understood that fibrillation patterns can be comprised of as many as a dozen or more competing activation wavefronts.

The objective of defibrillation is to generate a large enough electrical field across heart 10 so as to reset all of the heart cells that are involved in the fibrillation pattern. An implantable defibrillator generates this large electrical field by discharge an electrical countershock having a large current between electrodes 20, 22 positioned about the heart. In FIG. 1, a pair of large patch electrodes 20, 22 are shown attached to the exterior of heart 10, although it will be understood that many forms of electrodes such as catheter, subcutaneous patch, or ICD housing are capable of serving as electrodes for generating the requisite electrical field.

The electrical field must be large enough to accomplish two things. First, the electrical field must stimulate the vast majority of cells in heart 10, thereby beginning a new activation period for those cells such that the cells are resynchronized. Second, the electrical field must protect the cells in heart 10 from further stimulation by other cells which were not initially captured by the electrical field. Of special concern are cells which are only partially stimulated by the electrical field. Such cells did not receive enough of a charge from the electrical field to begin a new activation potential, but they have a residual charge that remains on their cell membranes and can subsequently cause a delayed response. This delayed response by the partially stimulated cells can sometimes reinitiate fibrillation.

As discussed in the background section of the application, the two basic kinds of truncated capacitive discharge waveforms which have been implemented by commercially approved implantable defibrillator systems are: monophasic waveforms and biphasic waveforms. Each of these waveforms approaches the problem of reinitiation of fibrillation due to partially stimulated heart cells in a somewhat different manner and it is helpful to understand these differences.

Figure 2:
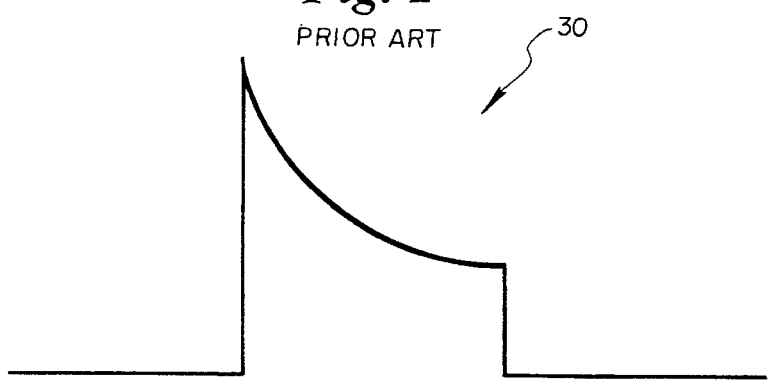
FIG. 2 is a graphic depiction of a monophasic defibrillation waveform.

A monophasic waveform 30 as shown in FIG. 2 approaches the problem of reinitiation of fibrillation by delivering a very large electrical countershock that leaves few, if any, partially stimulated heart cell which could later reinitiate fibrillation. To be of sufficient strength, monophasic waveform 30 must be sufficiently strong enough to capture nearly 100% of the heart cells and capture these cells so strongly that they are resistant to restimulation for a long period of time (i.e., they are in a refractory state for an extended period of time). In FIG. 2, the strength of monophasic waveform 30 can be evaluated by integrating the amount of charge delivered by monophasic waveform 30 (i.e., the amount of space under the curve of waveform 30) as a measure of the total energy delivered by waveform 30 to heart 10. With appropriate safety margins, the typical energy values used in commercially approved implantable defibrillators for delivery of monophasic waveforms 30 are in the range of 35–40 joules.

Figure 3:
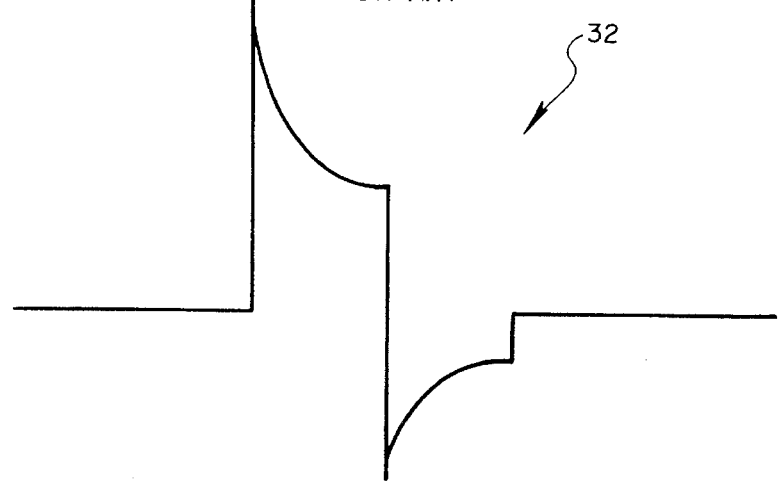
FIG. 3 is a graphic depiction of a biphasic defibrillation waveform.

A biphasic waveform 32 as shown in FIG. 3 approaches the problem of reinitiation of fibrillation by providing a second smaller and opposite polarity pulse 34 immediately after the initial countershock pulse 36. It is believed that this second phase 34 removes excess charge from the cell membranes of those cells which were only partially stimulated. By removing the excess charge from heart cells which were only partially stimulated, second phase 34 prevents those cells from reinitiating fibrillation. As a result, the total energy required for first phase 36 is reduced as it is no longer necessary for first phase 36 to capture 100% of the heart cells. For a more detailed discussion of this theory, reference is made to the previously identified related application entitled "METHOD AND APPARATUS FOR GENERATING BIPHASIC WAVEFORMS IN AN IMPLANTABLE DEFIBRILLATOR."

As shown by a comparison of FIG. 2 and FIG. 3, the total energy required for biphasic waveform 32 is significantly less than for monophasic waveform 30. Studies have demonstrated that energies required for successful defibrillation using biphasic waveforms can be as much as 25%–40% lower than those required when using monophasic waveforms. With appropriate safety margins, the typical energy values used in commercially approved implantable defibrillators for delivery of biphasic waveforms 32 are in the range of 25–35 joules.

Figure 4:
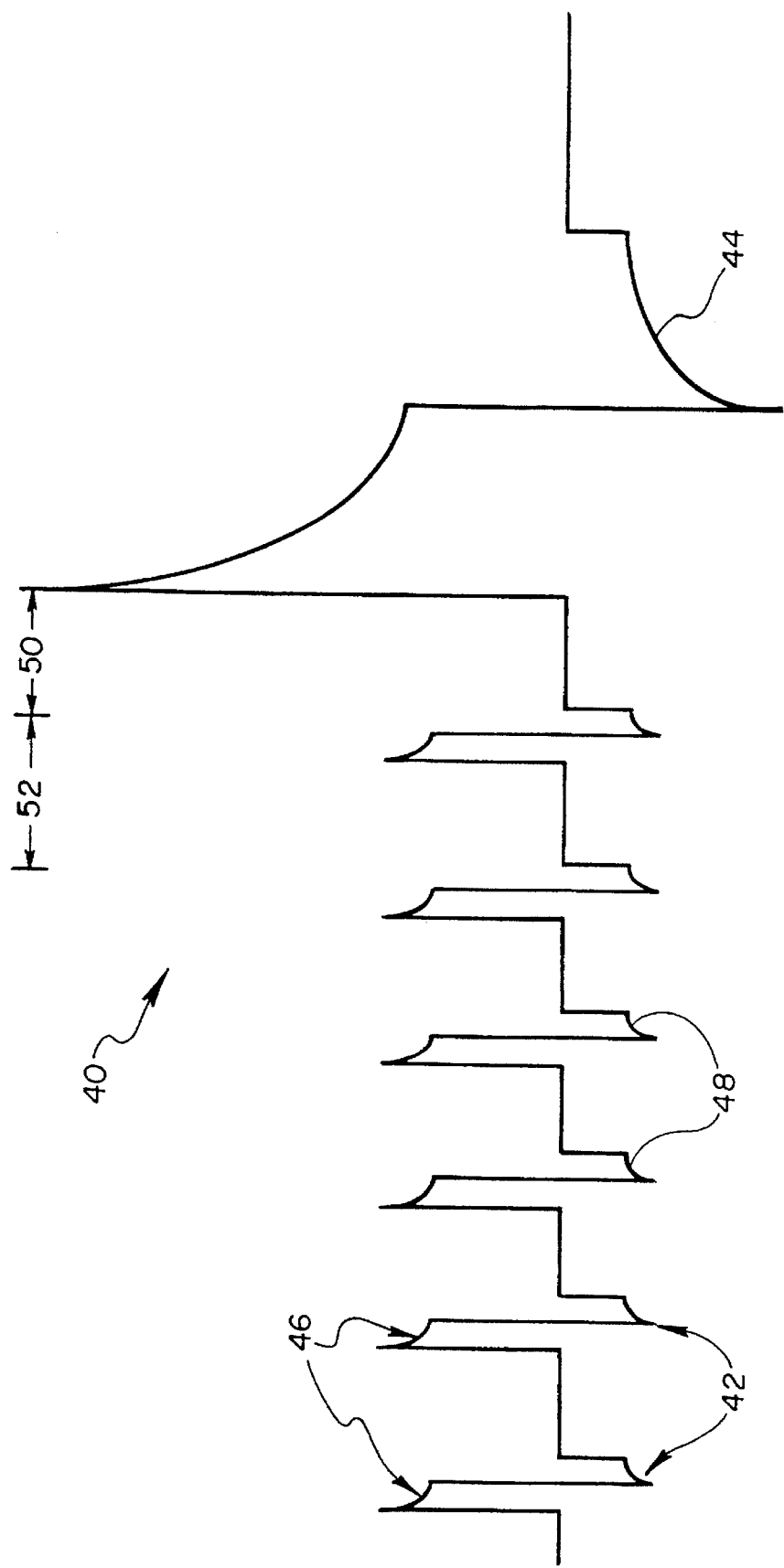
FIG. 4 is a graphic depiction of a multiple, discontinuous pulse waveform comprised of a series of smaller recruitment pulses followed by a larger defibrillating pulse.

In contrast to the monophasic and biphasic waveforms currently delivered by commercially approved implantable defibrillators which are a single, continuous pulse waveform, the present invention as shown in FIG. 4 delivers a multiple, discontinuous pulse waveform 40 that is comprised of a series of smaller recruitment pulses 42 delivered prior to delivery of a larger defibrillating pulse 44. In the same way in which biphasic waveform 32 decreases the overall energy required for defibrillation by operating after delivery of the defibrillating pulse to decrease the number of heart cells which must be completely captured, waveform 40 of the present invention decreases the overall energy required for defibrillation by operating before delivery of the defibrillating pulse to recruit or capture as many heart cells as possible into one of the activation wavefronts 12, 14. Unlike prior art attempts at multiple pulse waveforms, and unlike the triphasic waveform of Jones et al, the present invention recognizes that, even though the electrical activity of the heart is essentially chaotic during fibrillation, it is still possible to enhance coordination of an activation wavefront rhythm during fibrillation by using multiple smaller recruitment pulses 42 delivered over a period of time prior to delivery of a defibrillating pulse 44. Although recruitment pulses 42 are significantly larger than pacing pulses delivered from a pacemaker, recruitment pulses 42 are designed to have a pacing-like impact on activation wavefronts 12, 14 a fibrillating heart 10.

Figure 5:
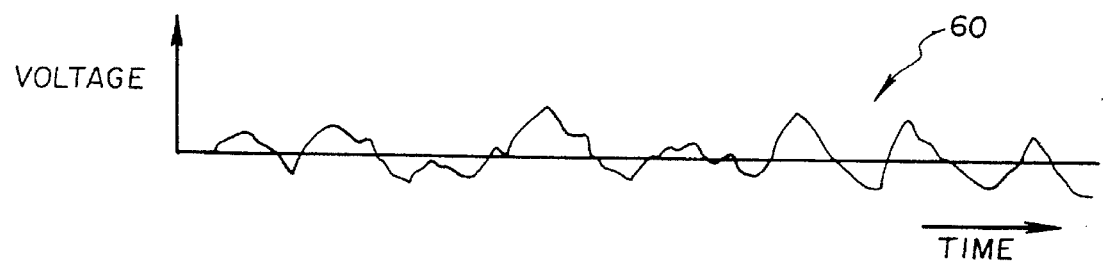
FIG. 5 is a plot of voltage as a function of time for fibrillation as seen by a pair of defibrillation electrodes.

To understand how recruitment pulses 42 of the present invention function, it is helpful to examine a plot of a voltage signal 60 as a function of time of the voltage seen, for example, between electrodes 20 and 22 of FIG. 1. An example of such a plot of voltage signal 60 is shown in FIG. 5. Although voltage signal 60 appears to be random and chaotic, it is possible to analyze signal 60 using advanced signal processing techniques, such as auto-correlation or fast fourier transform, for example, to establish an inherent frequency of voltage signal 60. Typically, it has been found that the inherent frequency of many fibrillation signals studied in this manner are in the range of 4 to 10 Hz with a corresponding fibrillation cycle length time in the range of 100 to 250 ms.

Unlike existing multiple pulse defibrillation techniques, such as those taught by Sweeney et al., which attempt to match a series of identical defibrillation pulses to the fibrillation cycle length for the purpose of extinguishing the fibrillation, the present invention preferably matches a series of smaller recruitment pulses 42 to the fibrillation cycle length for the purpose of coordinating activation wavefronts, such that a defibrillation pulse 44 of less energy can successfully convert the fibrillation. It is believed that less energy is required for defibrillation pulse 44 as compared to the energy required for a standard monophasic or biphasic defibrillation waveform because the activation wavefronts have been coordinated and synchronized by the series of recruitment pulses. With more generally coordinated activation wavefronts, it is now possible to time the delivery of defibrillation pulse 44 with phase 4 of the stimulation cycle of the heart cells in the primary activation wavefront. As heart cells in phase 4 require as little as one-tenth the energy to stimulate than in any other phase, less energy is required to capture all of the heart cells.

Figure 6:
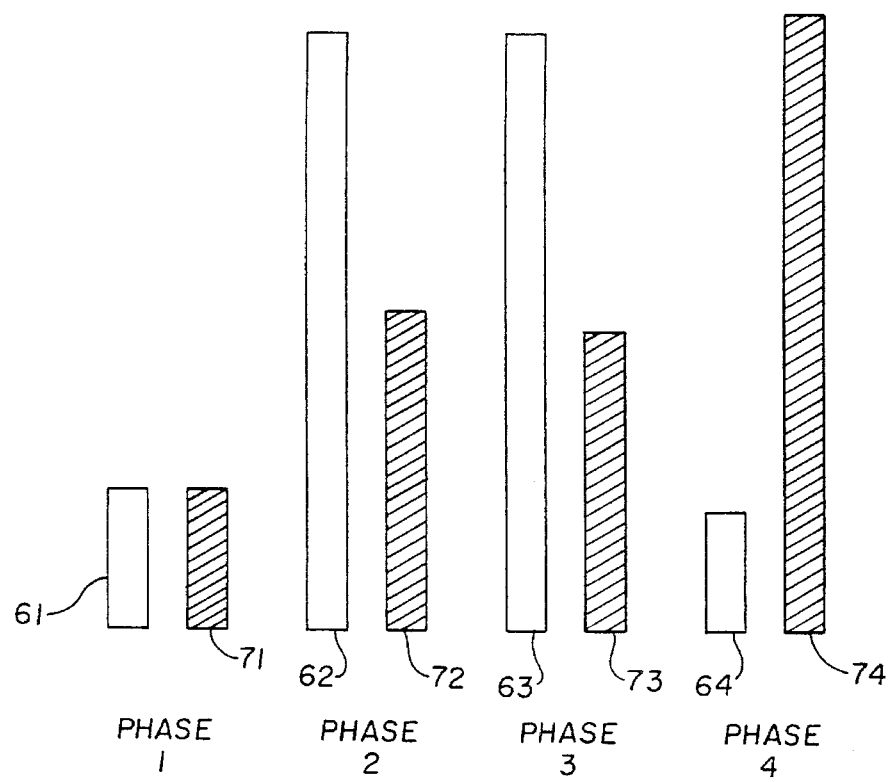
FIG. 6 is a graphic comparison of the percentage of heart cells in each of the four phases of stimulation for a normal fibrillating heart and for a fibrillating heart which has received a series of recruitment pulses in accordance with the present invention.

The importance of synchronizing the activation wavefronts 12, 14 of a fibrillating heart by utilizing the recruitment pulses in accordance with the present invention is graphically demonstrated by FIG. 6. FIG. 6 compares the percentage of heart cells of a fibrillating heart which are in each of the four phases of stimulation between an unrecruited fibrillation (61, 62 63 and 64) and a fibrillation which has been recruited in accordance with the present invention (71, 72, 73 and 74). In the former case, the percentage of heart cells in phase 1, as shown at 61, is essentially equal to the percentage of time that a single heart cell is in phase 1 stimulation. Similarly, the percentages of heart cells in phases 2, 3 and 4, as shown respectively at 62, 63 and 64, is essentially equal to the percentage of time that a single heart cell is in each of those phases. In contrast, for the recruited fibrillation, the percentage of heart cells in phases 1, 2 and 3 is decreased and the percentage of heart cells in phase 4 is increased when measured at the time at which phase 4 occurs relative to the inherent fibrillation cycle length time of the primary activation wavefront to which other heart cells have been recruited by the series of recruitment pulses 42.

Figure 7:
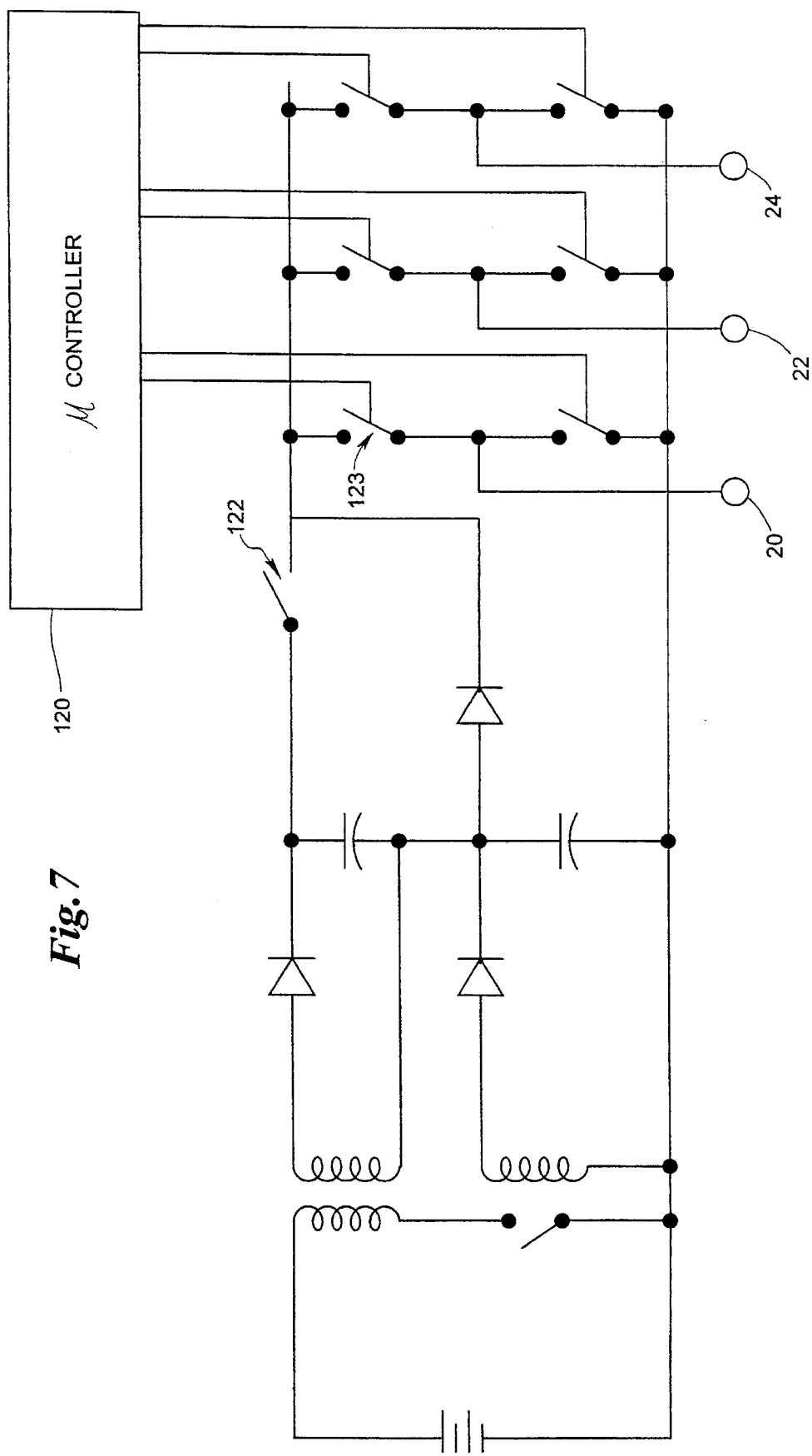
FIG. 7 shows a schematic diagram of a preferred embodiment of circuitry for controlling the selective capacitive discharge from an implantable defibrillator to create the multiple, discontinuous defibrillation waveform of the present invention.

FIG. 7 shows a schematic diagram of a preferred embodiment of circuitry for controlling the selective capacitive discharge from an implantable defibrillator to create the multiple, discontinuous defibrillation waveform of the present invention. The implantable defibrillator itself is a self-contained human implantable housing containing a battery 100 used to drive a current through the primary winding 102 of transformer 104 at a high frequency by the current interruption of switch 106. This results in high voltages being developed across the two secondaries 108, 110 of transformer 104. These high voltages are rectified by diodes 112 and 114 and stored in energy storage capacitors 116 and 118. For delivery of a defibrillation pulse 44, switch 122 is enabled, preferably under control of a microprocessor 120. A monophasic defibrillation pulse 44 may be delivered between electrodes 20, 22 by turning on switches 123 and 126. A biphasic defibrillation pulse 44 may be delivered between electrodes 20, 22 with the use of switches 124 and 125 to deliver the current from capacitors 116 and 118 in a negative direction. Similarly, switches 127 and 128 may be used in conjunction with the preceding switches (123–126) to deliver monophasic and/or biphasic defibrillation waveforms 44 through various electrode pathways among electrodes 20, 22 and 24, for example. To deliver the lower voltage recruitment pulses 42, switch 122 is disabled and a current is drawn through diode 130. The operation of all other components would remain the same. In either case, switches 123–128 are preferably controlled by microprocessor 120. For a more detailed description of the operation of microprocessor 120 and switches 123–128, reference is made to the previously identified copending application entitled "IMPLANTABLE CARDIOVERTER DEFIBRILLATOR SYSTEM HAVING INDEPENDENTLY CONTROLLABLE ELECTRODE DISCHARGE PATHWAYS." For a more detailed description of the operation of various combinations of the charging circuitry, including battery 100 and transformer 104, reference is made to the previously identified co-pending application entitled "SYSTEM AND METHOD FOR DELIVERING MULTIPLE CLOSELY SPACED DEFIBRILLATION PULSES."

Referring again to FIG. 4, a more detailed description of a preferred embodiment of recruitment pulses 42 is presented. For purposes of illustration of this preferred embodiment, it is assumed that each of capacitors 116 and 118 have been charged to a voltage of 300V. In this embodiment, each recruitment pulse 42 is delivered as a biphasic pulse having a first phase 46 delivered between the selected electrodes 20, 22 in a forward direction from the charge on capacitor 116 for a period of about 300 μs. At the end of first phase 46, microcontroller 120 toggles the appropriate switches 123–128 and current is drawn in a reverse direction from the charge on capacitor 116 for a period of about 200 μs to generate a second phase 48. Due to the short time period for each phase 46, 48, there is very little decay in the capacitor voltage during each recruit pulse. The small decay in the output voltage during each phase 46, 48 is due to the fact that capacitor 116 has a fairly high time constant, preferably greater than about 25 ms, and each of the phases 46, 48 are relatively short, preferably less than about 500 μs. As a result, each recruitment pulse 42 appears to the heart as closer to a rectangular biphasic pulse than the more traditional decaying biphasic pulse as shown in FIG. 2.

The total energy delivered by each recruitment pulse 42 is preferably less than a maximum recruitment charge value. This is necessary to insure that the implantable defibrillator can deliver the sequence of recruitment pulses 42 without detracting from the ability of capacitors 116, 118 to deliver an effective defibrillation pulse 44. In a preferred embodiment, the maximum recruitment charge value is determined by an amount of electrical charge which can be recharged in the time between delivery of the last recruitment pulse 42 and delivery of defibrillation pulse 44. Typical batteries 100 used for implantable defibrillators have power outputs of 6 W and the efficiencies of transformer 104 can deliver 4 W of that power output to charge capacitors 116, 118. Recruitment pulses 42, as shown in FIG. 4, have a per pulse energy of approximately 0.9J as given by the formula:

$E = V^2 \cdot d/r$ where V is the voltage, d is the total pulse duration and r is the interelectrode resistance (typically figured at 50 ohms). If, for example, four recruitment pulses 42 are delivered per second (matching a defibrillation cycle length of 4 Hz), the total energy required to be delivered would be 3.6J in one second, which is equal to 3.6 W. As the value of 3.6 W is less than the 4 W which can be sustainably recharged by battery 100 and transformer 104, the present invention is capable of easily sustaining delivery of these recruitment pulses 42 without detracting from the energy which is needed for defibrillation pulse 44.

The maximum amount of electrical charge which battery 100 and transformer 104 can recharge capacitors 116, 118 is referred to as the maximum recruitment charge and is set as an upper limit of the amount of energy delivered by each recruitment pulse 42. Because the charging circuitry delivers electrical charge as a function of time, it is also important to establish a time period 50 between the last recruitment pulse 42 and defibrillation pulse 44 as shown in FIG. 4. This time period 50 may be equal to, shorter than, or longer than the time periods 52 between successive recruitment pulses 42. Preferably, time period 52 is established to be synchronized with a fibrillation cycle length determined from a voltage plot, such as shown in FIG. 5, and with the highest peak within that fibrillation cycle length. It is believed that this highest peak represents the strongest of the activation wavefronts 12, 14 in a phase 1 activation. Recruitment pulses 42 act to recruit heart cells in other wavefronts to join in with the strongest of the activation wavefronts. Recruitment pulses 42 are most effective for heart cells located within the strongest electrical field of the pulse and for heart cells that are in an activation wavefront that is in phase 4 when the strongest activation wavefront is in phase 1. Time period 50 is preferably adjusted such that defibrillation pulse 44 is delivered when the strongest activation wavefront which has been further strengthened by recruitment pulses 42 is in phase 4 and is most susceptible to stimulation with the least amount of energy. In this way, the present invention can reduce the total energy required for defibrillation pulse 44 to effectively defibrillate heart 10. Preferably, the control circuitry of the present invention limits time periods 50 and 52 to between 25 milliseconds and 1 second.

First phase 46 of each recruitment pulse 42 is fairly narrow and is designed to stimulate a large number of cells without drawing excessive energy from capacitors 116, 118. Second phase 48 also has a narrow pulse width and is designed to remove any excess charge from the cell membranes to minimize the risk of partially stimulated cells from initiating another activation wavefront. Although recruitment pulse 42 is preferably a biphasic waveform, it is anticipated that many other continuous pulses could be used as the waveshape for each recruitment pulse, such as a monophasic pulse or even a triphasic pulse. In all cases, the initial discharge voltage is less than about one-half of the initial discharge voltage of defibrillation pulse 44 such that the pulses in the train of multiple pulses are not identical. In the preferred embodiment as described, it is assumed that capacitors 116 and 118 have an equal capacitance value and therefor recruitment pulses 42 have an initial discharge voltage value that is one-half of the initial discharge voltage value of defibrillation pulse 44.

In an alternative embodiment which utilizes the same circuitry as shown in FIG. 7, capacitors 116 and 118 may be chosen such that capacitor 118 would have a larger effective capacitance than capacitor 116. In this example, capacitor 116 could store 10J and have an effective capacitance of 125 μF with a charging voltage of 400V and capacitor 118 could also store 10J, but would have an effective capacitance of 500 μF and a charging voltage of only 200V. As a result, each recruitment pulse 42 delivered from capacitor 118 would have an initial discharge voltage of 200V. In this example, first phase 46 could be approximately 1 ms, due to the longer time constant of capacitor 118, and second phase 48 could be approximately 0.5 ms. This would produce a total energy for each recruitment pulse of 1J which at a delivery rate of 4 Hz would still be less than a maximum recruitment charge of 4 W. The advantage of this embodiment is that the pulse widths of each recruitment pulse are closer to optimum for cardiac stimulation. The disadvantage is that the approach requires capacitors 116 and 118 to be of different size and have different charging voltages.

Referring again to FIG. 4, a more detailed example of defibrillation pulse 44 is presented for when switch 122 in FIG. 7 is closed and thus the full voltage from capacitors 116 and 118 is delivered in series of the switching network of switches 123–128. In the case where each capacitor has a charging voltage of 300V, the initial discharge output voltage of defibrillation pulse 44 is 600V and discharges to about 200V over a duration of 3 ms, assuming an effective capacitance of capacitors 116 and 118 as combined in series of 60 μF (120 μF for each capacitor) and an effective inter-electrode resistance of 50 ohms. At this point, the current flow is reversed in the manner previously described and a negative phase of a duration of about 1.5 ms is delivered. In this example, the total energy required for defibrillation pulse 44 is about 11J, of which about 9.5J is actually delivered. When combined with a sequence of eight (8) recruitment pulses as about 1J per pulse, the total energy required for effective defibrillation is less than 20J, as compared with 25–40J for existing implantable defibrillators. More importantly, the size of battery 100, transformer 104 and capacitors 116 and 118 can be reduced because even though 20J are delivered over the entire multiple, discontinuous pulse waveform, only 11J need to be charged and stored for defibrillation pulse 44.

Figure 8:
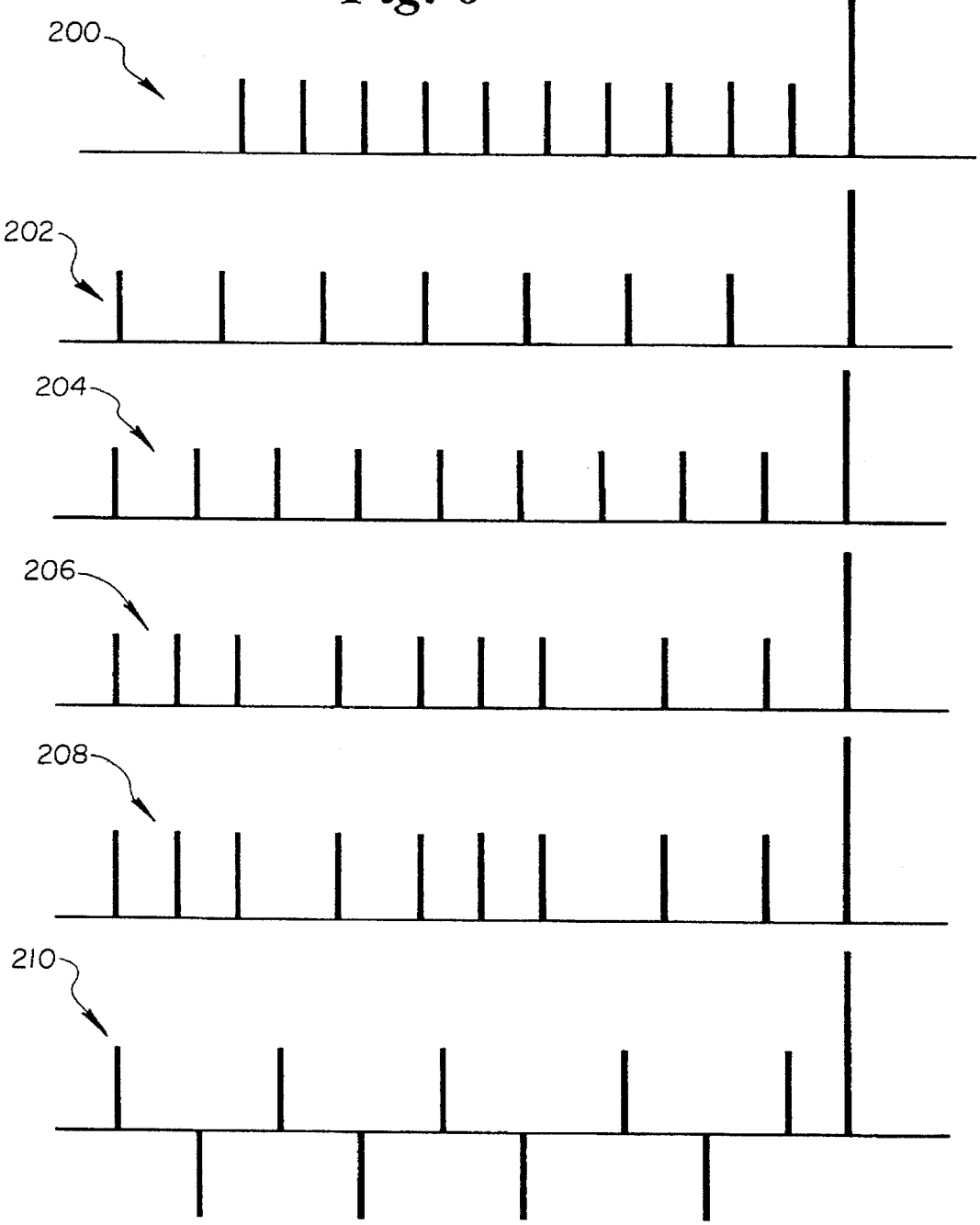
FIG. 8 shows in a simplified representation a number of alternative configurations for delivery of the multiple, discontinuous pulse waveform of the present invention.
Figure 10:
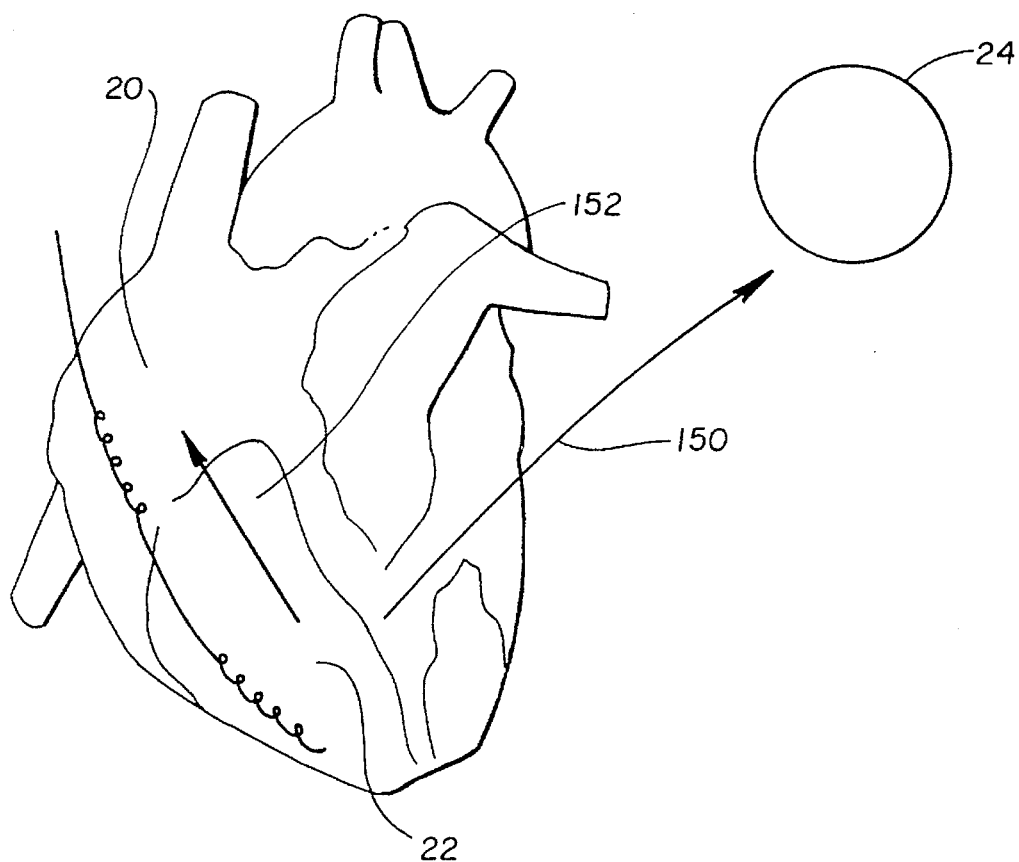
FIG. 10 is a schematic representation of multiple discharge pathways for the present invention.

FIG. 8 discloses a number of alternative configurations for delivery of the multiple, discontinuous pulse waveform of the present invention. In each waveform 130, 132, 134 and 136, the short vertical bars represent recruitment pulses 42 and the final tall vertical bar represents defibrillation pulse 44. In the first waveform 140, recruitment pulses 42 are timed at the maximum rate possible given the maximum recruitment charging value for the particular components involved. In the second waveform 142, recruitment pulses are timed are a predetermined rate that is representative of the intrinsic fibrillation cycle rate typically seen in fibrillation, i.e., something on the order of 4–5 Hz, which corresponds to a sinus heart rate of 240–300 beats per minute. In the third waveform 144, recruitment pulses are timed to an intrinsic fibrillation cycle rate determined from a voltage as sensed similar to FIG. 5. This determination can be accomplished by analyzing for zero crossings, zero crossings of the derivative or various spectral analysis techniques such as auto correlation. The spacing between successive recruitment pulses 42 is than set to some predefined fraction (e.g., 85%) of the intrinsic fibrillation cycle rate as initially determined. In the fourth waveform 146, the timing of recruitment pulses is dynamically varied in response to an instantaneous sensing and analysis of the intrinsic fibrillation cycle rate, such as from a separate bipolar sensing electrode. In the fifth waveform 148, the discharge pathway of successive recruitment pulses is selectively varied among multiple electrodes such that the initial recruitment pulse is delivered along electrode pathway 160 and the next recruitment pulse is delivered along electrode pathway 162, as shown in FIG. 10. In the sixth waveform 150, as shown in FIG. 8, the polarity of successive recruitment pulses is selectively changed such that the initial recruitment pulse has an initial positive polarity and the next recruitment pulse has an initial negative polarity. It will be apparent to those skilled in the art that numerous combinations of the foregoing can be selectively implemented in an implantable defibrillator by use of programmable control of microprocessor 120, for example.

Figure 9:
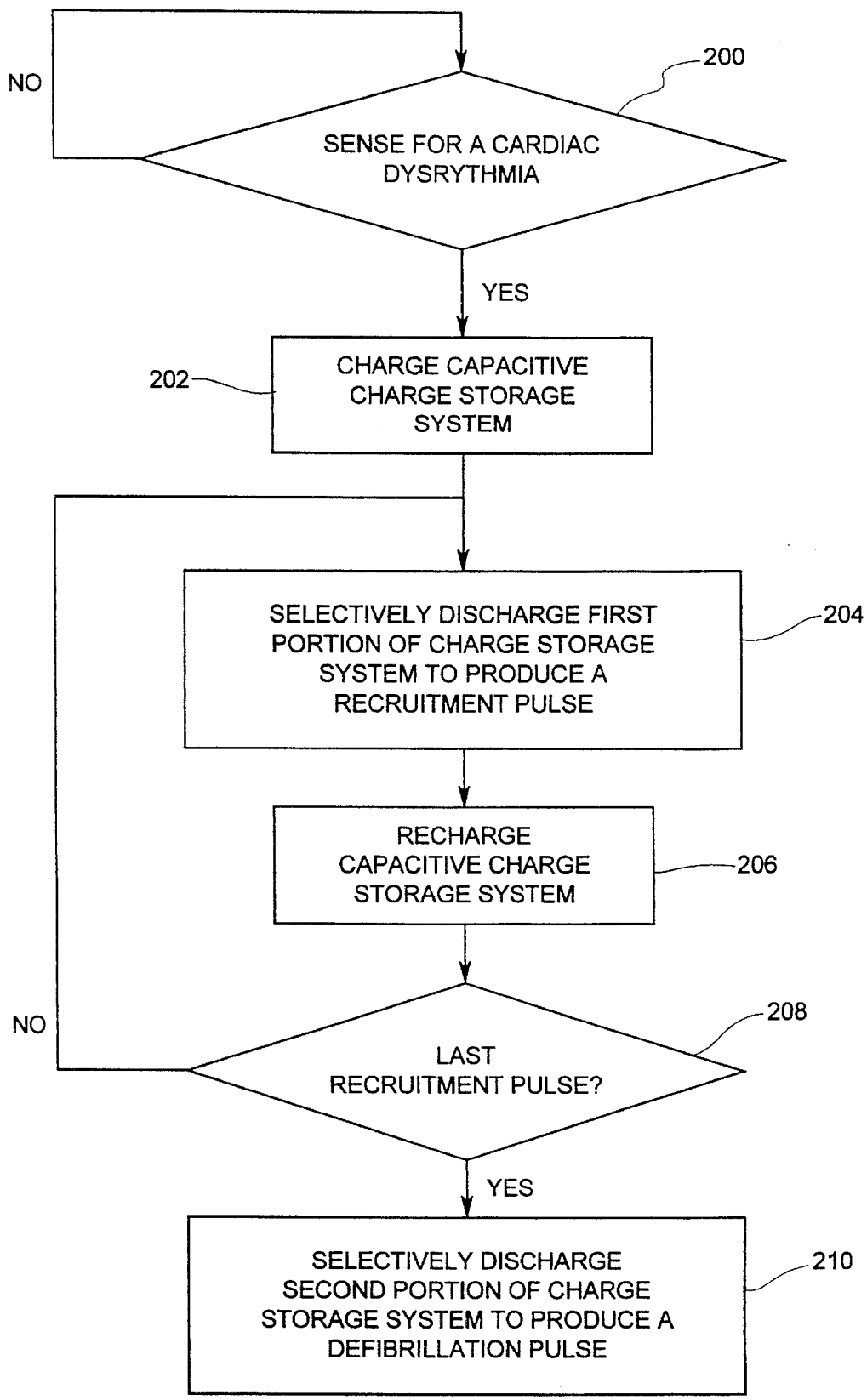
FIG. 9 is a flow chart of a preferred method of the present invention.

Referring now to FIG. 9, a detailed description of a preferred embodiment of the method of the present invention will be described. At step 200, an implantable defibrillator senses for a cardiac dysrhythmia in a human patient. At step 202, in response to sensing the cardiac dysrhythmia, the implantable defibrillator charges a capacitive charge storage system within the implantable defibrillator device to a charge value. At step 204, less than a first portion of the charge value stored in the capacitive charge storage system is selectively discharged through at least two electrodes adapted for implantation in the human patient to produce a plurality of recruitment pulses, each recruitment pulse spaced apart by a first time interval. At step 206, the capacitive charge storage system is recharged to the charge value after each recruitment pulse. At step 208, a check is made to see if the series of recruitment pulses have been delivered. If not, then process control returns to step 204. Finally, at step 210, when all of the recruitment pulses have been delivered, more than the first portion of the charge value stored in the capacitive charge storage system is selectively discharged through the at least two electrodes to produce a defibrillation pulse that is spaced apart by a second time interval from the plurality of recruitment pulses.

Although the description of the present invention has been presented in terms of a series of recruitment pulses having identical charges and, hence, identical recharging times, it is also possible to vary the charges in successive recruitment pulses, so long as the capacitive charge storage system is recharged to the intended charge value for delivery of a defibrillation pulse. The present invention should also be distinguished from a programmed therapy regimen for an implantable defibrillator in which a series of successive defibrillation waveforms are delivered to a patient in the event that initial defibrillation attempts are unsuccessful. It is intended that the present invention, as a single defibrillation waveform could comprise one of the series of successive waveforms of a programmed therapy regimen, however, a programmed therapy regimen should not be confused with the delivery of recruitment pulses followed by a defibrillation pulse in accordance with the present invention. In the present invention, it is anticipated that the entire defibrillation waveform would be delivered within less than about 1–2 seconds, whereas in a programmed therapy regimen, successive defibrillation countershocks are delivered over a period of 1–3 minutes with intervals between successive countershocks on the order of 20–40 seconds.

I claim:

1. An improved implantable defibrillator system for producing a multiple pulse capacitive-discharge countershock to be delivered through at least two electrodes adapted for implantation in a human patient, the implantable defibrillator system being a self-contained human implantable housing containing a waveform-generating capacitor means for storing an electrical charge, means for charging the waveform-generating capacitor means, means for sensing a cardiac dysrhythmia in the human patient, and means for selectively discharging the electrical charge in the waveform-generating capacitor means as a countershock to be delivered through the at least two electrodes in response to the means for sensing the cardiac dysrhythmia, the improvement comprising:

the means for selectively discharging including:
means for selectively discharging a plurality of recruitment pulses, each recruitment pulse spaced apart by a first time interval and delivering an electrical charge from the waveform-generating capacitor means that is less than a maximum recruitment charge; and
means for selectively discharging a defibrillation pulse spaced apart by a second time interval from the plurality of recruitment pulses and delivering an electrical charge that is greater than the maximum recruitment charge, wherein the maximum recruitment charge is determined by an amount of electrical charge which the charging means can recharge the waveform-generating capacitor means during the second time interval.

2. The implantable defibrillator system of claim 1 wherein the means for selectively discharging the plurality of recruitment pulses includes means for delivering at least one recruitment pulse as a biphasic pulse.

3. The implantable defibrillator system of claim 1 wherein the means for selectively discharging the plurality of recruitment pulses includes means for selectively varying a discharge pathway between the at least two electrodes for successive recruitment pulses.

4. The implantable defibrillator system of claim 1 wherein the means for selectively discharging the plurality of recruitment pulses includes means for reducing a discharge voltage of the recruitment pulses in relation to a charging voltage applied to the waveform-generating capacitor means by the means for charging.

5. The implantable defibrillator system of claim 1 wherein the means for selectively discharging the plurality of recruitment pulses includes means for selectively varying the first time interval between successive recruitment pulses.

6. The implantable defibrillator system of claim 5 wherein the means for sensing includes means for sensing a fibrillation rate and wherein the means for selectively varying the first time interval between successive recruitment pulses varies the first time interval based on a percentage of the fibrillation rate.

7. The implantable defibrillator system of claim 1 wherein the means for sensing includes means for sensing a fibrillation rate and wherein the means for selectively discharging the recruitment pulses includes means for establishing the first time interval between successive recruitment pulses based on a percentage of the fibrillation rate.

8. The implantable defibrillator system of claim 1 wherein the means for selectively discharging the plurality of recruitment pulses includes means for selectively varying a polarity of the recruitment pulses.

9. The implantable defibrillator system of claim 1 wherein the means for selectively discharging limits the first and second time intervals to between 25 milliseconds and 1 second.

10. A method for operating an implantable defibrillator device electrically connected to at least two electrodes adapted for implantation in a human patient to treat cardiac dysrhythmia by delivering a multiple pulse capacitive-discharge countershock, the method comprising the device-implemented steps of:

(a) sensing for a cardiac dysrhythmia in a human patient;

(b) in response to sensing the cardiac dysrhythmia, charging a capacitive charge storage system within the implantable defibrillator device to a charge value;

(c) selectively discharging less than a first portion of the charge value stored in the capacitive charge storage system through the at least two electrodes to produce a plurality of recruitment pulses, each recruitment pulse spaced apart by a first time interval;

(d) recharging the capacitive charge storage system to the charge value after each recruitment pulse; and (e) discharging more than the first portion of the charge value stored in the capacitive charge storage system through the at least two electrodes to produce a defibrillation pulse that is spaced apart by a second time interval from the plurality of recruitment pulses.

11. The method of claim 10 wherein the first portion of the charge value in step (c) is determined by an amount of electrical charge which step (d) can recharge the capacitive charging storage system during the second time interval.

12. The method of claim 10 wherein step (c) discharges the recruitment pulses as biphasic pulses.

13. The method of claim 10 wherein step (c) further includes the step of selectively varying a discharge pathway between the at least two electrodes for successive recruitment pulses.

14. The method of claim 10 wherein step (c) further includes the step of reducing a discharge voltage of the recruitment pulses in relation to a charging voltage applied to the capacitive charge storage system in steps (b) and (d).

15. The method of claim 10 wherein step (c) further includes the step of selectively varying the first time interval between successive recruitment pulses.

16. The method of claim 10 wherein step (a) senses a fibrillation rate and wherein step (c) further includes the step of selectively varying the first time interval between successive recruitment pulses based on a percentage of the fibrillation rate.

17. The method of claim 10 wherein step (c) further includes the step of selectively varying a polarity of the recruitment pulses.

18. The method of claim 10 wherein the first and second time intervals of step (c) and (e) are limited to between 25 milliseconds and 1 second.

19. The method of claim 10 wherein the capacitive charge storage system comprises at least two separate capacitor systems and wherein step (c) discharges less than the first portion of the charge value from a first capacitor system and step (e) discharges more than the first portion of the charge value from a second capacitor system.

20. The method of claim 19 wherein steps (b) and (d) charges the first capacitor system to a first discharge voltage and step (b) charges the second capacitor system to a second discharge voltage that is greater than the first discharge voltage.

21. An implantable defibrillator apparatus electrically connected to at least two electrodes adapted for implantation in a human patient to treat cardiac dysrhythmia by delivering a multiple pulse capacitive-discharge countershock, the implantable defibrillator apparatus comprising:

an implantable housing which contains:
  sensing means for sensing a cardiac dysrhythmia in the human patient;
  capacitor means for storing an electrical charge;
  power source means for charging the capacitor means to a charging voltage; and
  control means for selectively controlling the power source means and the capacitor means in response to the sensing of the cardiac dysrhythmia to deliver a multiple pulse capacitive-discharge countershock to the at least two electrodes including:
    means for selectively discharging a plurality of recruitment pulses, each recruitment pulse spaced apart by a first time interval and delivering an electrical charge that is less than a maximum recruitment charge; and
    means for selectively discharging a defibrillation pulse spaced apart by a second time interval from the plurality of recruitment pulses and delivering an electrical charge that is greater than the maximum recruitment charge.

22. The implantable defibrillator system of claim 21 wherein the means for selectively discharging the plurality of recruitment pulses includes means for delivering at least one recruitment pulse as a biphasic pulse.

23. The implantable defibrillator system of claim 21 wherein the means for selectively discharging the plurality of recruitment pulses includes means for selectively varying a discharge pathway between the at least two electrodes for successive recruitment pulses.

24. The implantable defibrillator system of claim 21 wherein the means for selectively discharging the plurality of recruitment pulses includes means for reducing a discharge voltage of the recruitment pulses in relation to a charging voltage applied to the waveform-generating capacitor means by the means for charging.

25. The implantable defibrillator system of claim 21 wherein the means for selectively discharging the plurality of recruitment pulses includes means for selectively varying the first time interval between successive recruitment pulses.

26. The implantable defibrillator system of claim 25 wherein the means for sensing includes means for sensing a fibrillation rate and wherein the means for selectively varying the first time interval between successive recruitment pulses varies the first time interval based on a percentage of the fibrillation rate.

27. The implantable defibrillator system of claim 21 wherein the means for sensing includes means for sensing a fibrillation rate and wherein the means for selectively discharging the recruitment pulses includes means for establishing the first time interval between successive recruitment pulses based on a percentage of the fibrillation rate.

28. The implantable defibrillator system of claim 21 wherein the means for selectively discharging the plurality of recruitment pulses includes means for selectively varying a polarity of the recruitment pulses.

29. The implantable defibrillator system of claim 21 wherein the means for selectively discharging limits the first and second time intervals to between 25 milliseconds and 1 second.

30. The implantable defibrillator system of claim 21 wherein the maximum recruitment charge is determined by an amount of electrical charge which the power source means can recharge the capacitor means during the longer of the second time interval.

31. The implantable defibrillator system of claim 21 wherein the capacitor means at least two separate capacitor systems and wherein the recruitment pulses are discharged from a first capacitor system and the defibrillation pulse is discharged from a second capacitor system.

32. The implantable defibrillator system of claim 31 wherein the first capacitor system is charged to a first discharge voltage and the second capacitor system is charged to a second discharge voltage that is greater than the first discharge voltage.

33. The implantable defibrillator system of claim 31 wherein the maximum recruitment charge is determined by an amount of electrical charge which the power source means can recharge the second capacitor system during shortest of the first time intervals.

* * * * *